(12) United States Patent
Yang et al.

(10) Patent No.: US 9,090,557 B2
(45) Date of Patent: Jul. 28, 2015

(54) METHOD FOR PRODUCING DI(2-ETHYLYHEXYL) TEREPHTHALATE

(71) Applicant: Chang Chun Plastics Co., Ltd, Taipei (TW)

(72) Inventors: Chung-Chi Yang, Taipei (TW); Yung-Shang Lin, Taipei (TW); Jing-Ping Wang, Taipei (TW); Shaw-Ming Du, Taipei (TW); Yih-Jiang Lai, Taipei (TW)

(73) Assignee: Chang Chun Plastics Co., Ltd., Taipei (TW)

( * ) Notice: Subject to any disclaimer, the term of this patent is extended or adjusted under 35 U.S.C. 154(b) by 0 days.

(21) Appl. No.: 14/149,199

(22) Filed: Jan. 7, 2014

(65) Prior Publication Data
US 2014/0288325 A1    Sep. 25, 2014

(30) Foreign Application Priority Data

Mar. 21, 2013    (TW) .............................. 102109993 U

(51) Int. Cl.
*C07C 67/08*    (2006.01)
*C07C 69/76*    (2006.01)

(52) U.S. Cl.
CPC ....................................... *C07C 67/08* (2013.01)

(58) Field of Classification Search
CPC .............................. C07C 67/08; C07C 69/76
USPC ............................. 562/412, 416; 560/98, 99
See application file for complete search history.

(56) References Cited

U.S. PATENT DOCUMENTS 4,788,172 A * 11/1988 Deardorff ..................... 502/167
7,276,621 B2 * 10/2007 Cook et al. ....................... 560/99

FOREIGN PATENT DOCUMENTS

| CN | 1225455 C | 11/2005 |
| JP | 2004-300078 | 10/2004 |

* cited by examiner

*Primary Examiner* — Kamal Saeed
*Assistant Examiner* — Janet L Coppins
(74) *Attorney, Agent, or Firm* — Muncy, Geissler, Olds & Lowe, P.C.

(57) ABSTRACT

Disclosed is a method for producing di(2-ethylhexyl)terephthalate (DOTP), which comprises subjecting terephthalic acid and 2-ethylhexanol to esterification in the presence of a chelate catalyst. The method of the present invention increases the reaction rate, improves the filtration efficiency of the ester product and yields DOTP with low APHA.

9 Claims, No Drawings

METHOD FOR PRODUCING DI(2-ETHYLHEXYL) TEREPHTHALATE

BACKGROUND OF THE INVENTION

1. Technical Field

The present invention relates to a method for producing di(2-ethylhexyl) terephthalate, and more particularly, to a method for producing di(2-ethylhexyl) terephthalate using a chelated catalyst of titanium or zirconium.

2. Background Technology

Di(2-ethylhexyl) terephthalate (also called diisooctyl terephthalate, DOTP for short) is a nontoxic plasticizer applicable to food containers and features good compatibility with polymeric materials such as polyvinyl chloride (PVC), low volatility, and excellent electric properties. DOTP may be prepared from 2-ethylhexanol and terephthalic acid (TPA) under pressurized conditions in the presence of a catalyst.

In the prior art, in order to increase the efficiency of esterification of terephthalic acid, for example, Japanese Patent Publication No. JP2004300078A, a technology is disclosed, where during the esterification for preparing terephthalic acid di-esters, a high boiling point solvent is used to increase the esterification temperature, which accelerates the esterification.

Furthermore, the aforesaid esterification of terephthalic acid is an equilibrium reaction; if the byproduct water produced in the production can be removed from the reaction, the equilibrium will remove towards the product side (i.e. ester side); and if water is not removed from the reaction system during the reaction, not only the catalyst is deactivated, but also the reaction becomes very slow after the equilibrium movement reaches a certain conversion rate. To solve this problem, for example, Chinese Patent CN1225455C disclosed a method for producing polybasic acid esters, where in the reaction zone in the presence of an esterification catalyst, an acid or its anhydride and an alcohol component are heated, and during the reaction, the vapor containing the alcohol and water is separated into an alcohol rich distillate and a water rich distillate by vapor distillation. The alcohol rich distillate is returned back to the reaction zone and the water rich distillate exits the reaction process. As such, the essentially quantitative conversion rate can be rapidly adjusted.

Currently, good methods for preparing DOTP are still badly needed and have yet to be further developed.

BRIEF SUMMARY OF THE INVENTION

The above mentioned methods still have some problems to be solved, such as elevating the reaction efficiency and improving the filtration rate of the ester product. Thus, the present invention provides a method for producing di(2-ethylhexyl) terephthalate, comprising: in an inert atmosphere, at a reaction pressure of higher than 1 atmosphere and a reaction temperature of 180-260° C., in the presence of a chelated catalyst of formula (I), subjecting terephthalic acid and 2-ethylhexanol to esterification,

$$(RO)_m T\text{-}(O\text{—}Y\text{—}X)_n \qquad (I),$$

wherein in the formula (I), R is hydrogen or $C_1$-$C_8$ linear or branched alkyl, T is titanium or zirconium, Y is $C_2$-$C_3$ alkylene or a divalent phosphate radical, X is a functional group containing oxygen or nitrogen, m is an integer of 1 or 2, and n is an integer of 2 or 3. By using the chelated catalyst, the method of the present invention elevates the reaction efficiency of esterification, improves the filtration rate of the ester product and obtains DOTP with low APHA.

In a preferable embodiment, the chelated catalyst is phosphate titanate chelate, triethanolamine titanate, or butyl titanium trialkoxyl phosphate dimer, wherein the content of titanium or zirconium in the chelated catalyst is 20 ppm to 400 ppm relative to the total weight of the reactants.

Furthermore, the reactor used in the method of the present invention is equipped with a condenser and an oil-water separator. In a preferable embodiment, the reactor is equipped with a return pipe; therefore, the mixture of water and alcohol produced by the esterification is condensed and separated in the oil-water separator, and the alcohol solution flows back to the reactor through the return pipe. Therefore, the molar ratio of the alcohol and the terephthalic acid remains a specific ratio in the reactor, and by measuring the removed water from the reactor, the conversion rate of the terephthalic acid can be calculated.

According to the method of the present invention, the 2-ethylhexanol is a pure 2-ethylhexanol or a 2-ethylhexanol recovered from the reaction that is not dehydrated. As the letter case, if the 2-ethylhexanol contains water, it can be used directly without removing water. The molar ratio of the 2-ethylhexanol to the terephthalic acid is 2.6:1 to 4.0:1, preferably, 3.0:1 to 3.5:1. The reaction pressure is above 1 atmosphere to 4.0 kg/cm² gauge pressure, wherein the pressure may be formed by nitrogen pressurization or by heating in an inter atmosphere to improve pressure naturally. Preferably, nitrogen pressurization is used.

In a preferable embodiment of the present invention, the esterification process is conducted at a temperature of 180 to 260° C., more preferably 200 to 250° C.

The method for producing di(2-ethylhexyl) terephthalate of the present invention uses the chelated catalyst of formula (I) to elevate the reaction efficiency, also improve the filtration rate of the ester product and yield DOTP with low APHA. In addition, using the method of the present invention, it is not necessary to equip complicated fractionation column with the reactor, but only condenser and oil-water separator are used to condense and separate the resultant water. Thus, deactivation of the catalyst is prevented and reduction of reaction time is achieved. Also, the fractionation column can be equipped if it does not impair the effect of the present invention.

DESCRIPTION OF THE PREFERRED EMBODIMENT

The main objective of the present invention is to provide a method for producing di(2-ethylhexyl) terephthalate, which features simple equipment, increases the esterification reaction rate and the filter efficiency. The method for producing di(2-ethylhexyl) terephthalate of the present invention is carried out in a reaction zone comprising a pressure vessel. Meanwhile, in order that the esterification proceeds smoothly, it is preferred to use the alcohol component in an excessive amount that exceeds the molar weight of the acid component. The molar ratio of 2-ethylhexanol to terephthalic acid is 2.6:1 to 4.0:1, preferably 3.0:1 to 3.5:1.

In an aspect, the present invention is characterized in that, in this production method, a chelated catalyst of formula (I) as shown below is used to subject terephthalic acid and 2-ethylhexanol to esterification,

$$(RO)_m T\text{-}(O\text{—}Y\text{—}X)_n \qquad (I),$$

wherein in the formula (I), R is hydrogen or $C_1$-$C_8$ linear or branched alkyl, T is titanium or zirconium, Y is $C_2$-$C_3$ alkylene or a divalent phosphate radical, X is a functional group containing oxygen or nitrogen, m is an integer of 1 or 2, and n is an integer of 2 or 3.

Representative chelated catalysts include, for example: phosphate titanate chelate, isopropyl tri(triethanolamine) titanate, butyl titanium trialkoxyl phosphate dimer, dihydroxyl (ammonium 2-hydroxypropionate) titanate chelate, diisopropyl di(dioctylphosphate) titanate chelate, ethylene bis(dioctylpyrophosphate) titanate chelate, isopropyl tri(dioctylphosphate) titanate chelate, dipropyl bis(glutarate) titanate chelate, diisobutyl di(triethanolamine) titanate chelate, diisopropyl di(acetylacetone) titanate chelate, dibutyl bis (ethyl acetylacetonate) titanate chelate, diisopropyl bis(triethanolamine) titanate chelate, butyl isopropyl di(acetylacetonate) titanate chelate, dibutyl di(ethyl acetoacetate) titanate chelate, diisopropyl di(ethyl acetoacetate) titanate chelate, isopropyl tri(dioctylphosphato) titanate chelate, isopropyl tri(dioctyl pyrophosphate) titanate chelate, diisopropyl di(triethanolamine) titanate chelate, diisopropyl di(diethyl citrate) zirconate chelate, diisopropyl di(triethanolamine) zirconate chelate, isopropyl tri(triethanolamine) zirconate chelate, and dihydroxyl (ammonium 2-hydroxypropionate) zirconate chelate.

As an effective amount of catalyst, the content of titanium or zirconium in the chelated catalyst of formula (I) is 20 ppm to 400 ppm relative to the total weight of the reactants, such that neutralization is not required until the esterification stage and even the end of the process; also, it is characterized by an excellent hue (platinum-cobalt) of ≤30 with a high conversion rate and a high conversion rate of the product with a low acid value of <0.1 mgKOH/g.

In the method of the present invention, the esterification proceeds at a temperature of 180-260° C., more preferably 200-250° C., and most preferably 230-250° C. If the esterification temperature is below the lower limit of 200° C., the esterification has a low rate and is not complete; if the reaction temperature is above the upper limit of 260° C., the monohydric alcohol is susceptible to decomposition which results in side reactions. The esterification stage is at least carried out higher than 1 atmosphere, or under a gauge pressure of more than 1.0 kg/cm$^2$, preferably 1.0-4.0 kg/cm$^2$. The pressure is produced by nitrogen pressurization or by heating in a nitrogen atmosphere naturally, and nitrogen pressurization is preferred. The esterification time is about 120-360 min, preferably 150-250 min.

Any common heatable reactors are applicable to the method of the present invention, such as a stirred tank reactor. Additionally, in order to thoroughly separate out the water produced in the esterification to avoid the deactivation of the catalyst and increase the conversion rate, in another aspect, the present invention is characterized in that, a complicated distillation column (fractionating column) is not required, but the reactor is equipped with an oil-water separator so that the vapor containing alcohol and water is condensed and separated in the oil-water separator. In a preferred embodiment, the reactor is equipped with a return pipe. For the esterification, the alcohol solution flows back to the reactor through the return pipe, so that the molar ratio of alcohol to terephthalic acid in the reactor remains constant to further take part in the esterification, and the separated water is removed from the reactor and metered to measure the conversion rate of terephthalic acid.

In another aspect, the present invention is characterized in that, the crude ester product of the aforesaid esterification is vacuumized and purified to afford a product with high purity, good hue, and low acid value. This purification process may be carried out either by evaporation in a thin film evaporator in the aforesaid esterification reactor or in an additional distillation column, or by filtering using filter paper. The vacuumization is carried out continuously under a vacuum degree of <2 mmHg and at a temperature of <240° C.; if the vacuum degree is >2 mmHg, the recovery rate is slow; if the temperature is >240° C., the product has poor hue, increased acid value and poor processability due to the fact that di(2-ethylhexyl) terephthalate is decomposed as a result of high temperature.

Above all, it is believed that the method of the present invention is characterized by subjecting terephthalic acid and 2-ethylhexanol to esterification, vacuumization, and purification in the presence of the aforesaid catalyst of formula (1), which increases the reaction rate, improves the filter efficiency of the ester, and provides a di(2-ethylhexyl) terephthalate product having a low hue (platinum-cobalt) of ≤30 and a low acid value of <0.1 mgKOH/g.

The present invention is to be further described through the following examples, but these examples are only for the purpose of illustration rather than limiting the scope of the present invention.

EXAMPLE

Example 1

To a 3 L high pressure reactor equipped with a stirrer, a thermometer, a foot valve pressure gauge, an oil-water separator, a return pipe, a nitrogen flow controller, a condenser, and a 30 cm filled distillation column, 1333.2 g (10.24 mole) of isooctanol (also called 2-ethylhexanol, 2-EH), 531.5 g (3.20 mole) of pure terephthalic acid (PTA), 3.07 g (Ti=82 ppm relative to the total weight of the alcohol and acid reactants in the reaction system) of Tyzor PC-64 catalyst (phosphate titanate chelate, Ti=5.0%, purchased from DORF KETAL CO.) were added. The reactor was fully stirred in a nitrogen flow and pressurized to a gauge pressure of 4.0 kg/cm$^2$, such that the temperature was allowed to increase to 232° C. (initial esterification cut-point) in 1 hr. The water and alcohol mixture carried out by the nitrogen flow was passed through the filled distillation column and the condenser and then condensed in the oil-water separator. The upper alcohol mixture was directed back to the reactor via the return pipe so as to ensure the 2-EH/PTA of the reaction system be maintained at a fixed molar ratio of 3.2/1, and the lower water was continuously distilled off and removed from the oil-water separator for metering. After the reaction continued at 232° C. for 0.6 hrs, the reaction was further heated to 250° C. to react for additional 5 hrs, and then the water was removed from the separator and metered as 114.0 ml (theoretical value 99.0%). The reactor was slowly depressurized to normal pressure, the temperature of the reaction system was 235° C., and 205.9 g of 2-EH were collected through the condenser. The acid value of the di-ester in the resultant crude reactants was 0.05 mg KOH/g, and the esterification lasted for 5.6 hrs in total. Next, the crude ester product was depressurized from 100 mmHg to a vacuum degree of <1 mmHg gradually to continuously distill off the unreacted alcohol at a distillation temperature of 180-190° C. After the vacuum degree reached <1 mmHg, the reaction lasted for 0.5 hrs, and then the reaction was depressurized to obtain 1208 g of a crude DOTP product. 500 g of the crude DOTP product were taken and passed through Whatman #5 filter paper, and the filtering lasted for 45 min and 19 sec, thereby obtaining an odorless product having a hue (platinum-cobalt) (measured according to the method set forth in ASTM D-1209) of 12 and an acid value of 0.03.

Example 2

The same reactor and reactant compounds as in Example 1 were used, but the filled distillation column was replaced by a 30 cm single column, and the catalyst was Tyzor TE (diisopropyl di(triethanolamine) titanate chelate, Ti=8.2%, purchased from DORF KETAL CO.). 1333.2 g (10.24 mole) of 2-EH, 531.5 g (3.20 mole) of PTA, and 1.87 g of Tyzor TE (Ti=82 ppm) were added to the reactor. The reactor was fully stirred in a nitrogen flow and pressurized to a gauge pressure of 4.0 kg/cm$^2$, such that the temperature was allowed to increase to 233° C. in 1 hr. The water and alcohol mixture carried out by the nitrogen flow was passed through the single column (meaning a filler free column) and the condenser and then condensed in the oil-water separator. The upper alcohol mixture was directed back to the reactor via the return pipe so as to ensure the 2-EH/PTA of the reaction system be maintained at a fixed molar ratio of 3.2/1, and the lower water was continuously distilled off and removed from the oil-water separator for metering. After the reaction continued at 232° C. for 0.6 hrs, the reaction was further heated to 250° C. to react for additional 3 hrs, and then the water was removed from the separator and metered as 114 ml (theoretical value 99.0%). The reactor was slowly depressurized to normal pressure, the temperature of the reaction system was 236° C., and 225 g of 2-EH were collected through the condenser. The acid value of the crude ester product was 0.10 mg KOH/g, and the esterification lasted for 3.7 hrs. Next, the crude ester product was depressurized from 100 mmHg to a vacuum degree of <2 mmHg gradually to continuously distill off the unreacted alcohol at a distillation temperature of 180-190° C. After the vacuum degree reached <2 mmHg, the reaction lasted for 0.5 hrs, and then the reaction was depressurized. After filtering lasted for 9 min and 17 sec, thereby obtaining an odorless product of 1233 g DOTP having a hue (platinum-cobalt) of 22 and an acid value of 0.08.

Example 3

The same reactor as in Example 1 was used, but the filled distillation column was replaced by a 30 cm single column, and the catalyst was Tyzor IAM (butyl titanium trialkoxyl phosphate dimer, Ti=8.8%, purchased from DORF KETAL CO.). 1333.2 g (10.24 mole) of 2-EH, 531.5 g (3.20 mole) of PTA, and 1.68 g (Ti=82 ppm) of Tyzor IAM were added to the reactor. The reactor was fully stirred in a nitrogen flow and pressurized to a gauge pressure of 3.0 kg/cm$^2$, such that the temperature was allowed to increase to 227° C. in 1 hr. The water and alcohol mixture carried out by the nitrogen flow was passed through the filled distillation column and the condenser and then condensed in the oil-water separator. The upper alcohol mixture was directed back to the reactor via the return pipe so as to ensure the 2-EH/PTA of the reaction system be maintained at a fixed molar ratio of 3.2/1, and the lower water was continuously distilled off and removed from the oil-water separator for metering. The reaction was further heated to 250° C. to react for additional 3.7 hrs, and then the water was removed from the separator and metered as 116.0 ml (theoretical value 100.7%). The reactor was slowly depressurized to normal pressure, the temperature of the reaction system was 242° C., and 175 g of 2-EH were collected through the condenser. The acid value of the di-ester in the resultant crude reactants was 0.08 mg KOH/g, and the esterification lasted for 4.0 hrs in total. Next, the crude ester product was depressurized from 100 mmHg to a vacuum degree of <2 mmHg gradually to continuously distill off the unreacted alcohol at a distillation temperature of 180-190° C. After the vacuum degree reached <5 mmHg, the reaction lasted for 0.5 hrs, and was continued by filtering lasted for 4 min and 5 sec, thereby obtaining 1227 g of an odorless DOTP having a hue (platinum-cobalt) of 25 and an acid value of 0.08.

Example 4

To a 3 L high pressure reactor equipped with a stirrer, a thermometer, a foot valve pressure gauge, an oil-water separator, a return pipe, a nitrogen flow controller, a condenser, and a 30 cm filled distillation column, 746 g (2.7 mole) of DOTP, 800 g (6.15 mole) of 2-EH, 319 g (1.92 mole) of PTA and 3.07 g (Ti=82 ppm) of Tyzor PC-64 catalyst were added. The reactor was fully stirred in a nitrogen flow and pressurized to a gauge pressure of 4.0 kg/cm$^2$, such that the temperature was allowed to increase to 248° C. in 1 hr. The water and alcohol mixture carried out by the nitrogen flow was passed through the filled distillation column and the condenser and then condensed in the oil-water separator. The upper alcohol mixture was directed back to the reactor via the return pipe so as to ensure the 2-EH/PTA of the reaction system be maintained at a fixed molar ratio of 3.2/1, and the lower water was continuously distilled off and removed from the oil-water separator for metering. Then, the reaction was further heated to 250° C. to react for additional 3.8 hrs, and then the water was removed from the separator and metered as 69.0 ml (theoretical value 99.7%). The reactor was slowly depressurized to normal pressure, the temperature of the reaction system was 235° C., and 205.9 g of 2-EH were collected through the condenser. The acid value of the di-ester in the resultant crude reactants was 0.06 mg KOH/g, and the esterification lasted for 4.3 hrs in total. Next, the crude ester product was depressurized from 100 mmHg to a vacuum degree of <2 mmHg gradually to continuously distill off the unreacted alcohol at a distillation temperature of 180-190° C. After the vacuum degree reached <2 mmHg, the reaction lasted for 0.5 hrs, and then the reaction was depressurized to obtain 1528 g of a crude DOTP product. 500 g of the crude DOTP product were taken and passed through Whatman #5 filter paper, and the filtering lasted for 10 min and 12 sec, thereby obtaining an odorless product having a hue (platinum-cobalt) of 20 and an acid value of 0.06.

Example 5

The same reactor as in Example 1 was used, but the filled distillation column was replaced by a 30 cm single column, and the catalyst was Tyzor IAM. 1333.2 g (10.24 mole) of 2-EH, 531.5 g (3.20 mole) of PTA, and 1.68 g (Ti=82 ppm) of Tyzor IAM were added to the reactor. The reactor was fully stirred in a nitrogen flow and pressurized to a gauge pressure of 4.0 kg/cm$^2$, such that the temperature was allowed to increase to 230° C. in 0.8 hr. The water and alcohol mixture carried out by the nitrogen flow was passed through the filled distillation column and the condenser and then condensed in the oil-water separator. The upper alcohol mixture was directed back to the reactor via the return pipe so as to ensure the 2-EH/PTA of the reaction system be maintained at a fixed molar ratio of 3.2/1, and the lower water was continuously distilled off and removed from the oil-water separator for metering. The reaction was carried out for 0.5 hours and further heated to 250° C. to react for additional 2.7 hrs, and then the water was removed from the separator and metered as 114.5 ml (theoretical value 99.4%). The reactor was slowly depressurized to normal pressure, the temperature of the reaction system was 242° C., and 188 g of 2-EH were collected through the condenser. The acid value of the di-ester in the resultant crude reactants was 0.10 mg KOH/g, and the esterification lasted for 2.7 hrs in total. Next, the crude ester product was depressurized from 100 mmHg to a vacuum degree of <2 mmHg gradually to continuously distill off the unreacted alcohol at a distillation temperature of 180-190° C. After the vacuum degree reached <2 mmHg, the reaction lasted for 0.5 hrs, and was continued by filtering lasted for 6 min and 43 sec, thereby obtaining 1235 g of an odorless DOTP having a hue (platinum-cobalt) of 25 and an acid value of 0.08.

Comparative Example 1

To a 3 L glass reactor equipped with a stirrer, a thermometer, an oil-water separator, a return pipe, a nitrogen flow meter, a condenser, and a 30 cm filled distillation column, 1000.0 g (7.68 mole) of 2-EH, 531.5 g (3.20 mole) of PTA, 3.14 g of Tytan TBT catalyst (tetra-n-butyl titanate, Ti=280 ppm, purchased from Borica) were added. The reactor was fully stirred in a nitrogen flow and heated to 178° C. in 0.7 hrs under normal pressure. The water and alcohol mixture carried out by the nitrogen flow was passed through the filled distillation column and the condenser and then condensed in the oil-water separator. The upper alcohol mixture was directed back to the reactor via the return pipe so as to ensure the 2-EH/PTA of the reaction system be maintained at a fixed molar ratio of 2.4/1, and the lower water was continuously distilled off and removed from the oil-water separator for metering. After the reaction continued for 5 hrs, the reaction was heated to 240° C., and then the water was removed from the separator and metered as 116 ml (theoretical value 100.7%). The acid value of the crude ester product of the reaction system was 0.11 mg KOH/g, and the esterification lasted for 5.0 hrs. Next, the crude ester product was depressurized from 100 mmHg to a vacuum degree of <2 mmHg gradually to continuously distill off excessive alcohols at a temperature of 180-190° C. After the vacuum degree reached <2 mmHg, the reaction lasted for 0.5 hrs, and then the reaction was depressurized to obtain 1235 g of a crude DOTP product. 500 g of the crude DOTP product were taken and passed through Whatman #5 filter paper, and the filtering lasted for 57 min and 38 sec, thereby obtaining an odorless product having a hue (platinum-cobalt) of 45 and an acid value of 0.10.

Comparative Example 2

To a 3 L glass reactor equipped with a stirrer, a thermometer, an oil-water separator, a return pipe, a nitrogen flow meter, a condenser, and a 30 cm filled distillation column, 613 g (2.22 mole) of DOTP, 600.2 g (4.61 mole) of 2-EH, 319 g (1.92 mole) of PTA, 1.81 g of Tytan TBT catalyst (Ti=165 ppm) were added. The reactor was fully stirred in a nitrogen flow and heated to 192° C. in 0.5 hrs under normal pressure. The water and alcohol mixture carried out by the nitrogen flow was passed through the filled distillation column and the condenser and then condensed in the oil-water separator. The upper alcohol mixture was directed back to the reactor via the return pipe so as to ensure the 2-EH/PTA of the reaction system be maintained at a fixed molar ratio of 2.4/1, and the lower water was continuously distilled off and removed from the oil-water separator for metering. After the reaction continued for 3 hrs, the reaction was heated to 250° C. for 1.4 hours, and then the water was removed from the separator and metered as 68.5 ml (theoretical value 100.1%). The acid value of the crude ester product of the reaction system was 0.11 mg KOH/g, and the esterification lasted for 4.4 hrs. Next, the crude ester product was depressurized from 100 mmHg to a vacuum degree of <2 mmHg gradually to continuously distill off excessive alcohols at a temperature of 180-190° C. After the vacuum degree reached <2 mmHg, the reaction lasted for 0.5 hrs, and then the reaction was depressurized to obtain 1235 g of a crude DOTP product. 500 g of the crude DOTP product were taken and passed through Whatman #5 filter paper, and the filtering lasted for 135 min and 30 sec, thereby obtaining a slightly cloudy product having a hue (platinum-cobalt) of 45 and an acid value of 0.11.

Comparative Example 3

The same reactor as in Example 1 was used, 1333.2 g (10.24 mole) of 2-EH, 531.5 g (3.20 mole) of PTA, 3.73 g of Tytan TBT catalyst (Ti=280 ppm) were added. The reactor was fully stirred in a nitrogen flow and pressurized to a gauge pressure of 4.0 kg/cm$^2$, such that the temperature was allowed to increase to 228° C. in 1 hr. The water and alcohol mixture carried out by the nitrogen flow was passed through the filled distillation column and the condenser and then condensed in the oil-water separator. The upper alcohol mixture was directed back to the reactor via the return pipe so as to ensure the 2-EH/PTA of the reaction system be maintained at a fixed molar ratio of 3.2/1, and the lower water was continuously distilled off and removed from the oil-water separator for metering. Then, the reaction was further heated to 250° C. to react for additional 5 hrs, and then the water was removed from the separator and metered as 112 ml (theoretical value 97.2%). The reactor was slowly depressurized to normal pressure, the temperature of the reaction system was 242° C., and 168 g of 2-EH were collected through the condenser. The acid value of the di-ester in the resultant crude reactants was 2.58 mg KOH/g, and the esterification lasted for 6.0 hrs in total. The reaction was continued for 1 hour and the resultant crude reactants was 0.08 mg KOH/g. Next, the crude ester product was depressurized from 100 mmHg to a vacuum degree of <2 mmHg gradually to continuously distill off the unreacted alcohol at a distillation temperature of 180-190° C. After the vacuum degree reached <2 mmHg, the reaction lasted for 0.5 hrs, and then the reaction was depressurized and filtered for 131 minutes and 4 seconds to obtain 1227 g of a slightly cloudy product having a hue (platinum-cobalt) of 35 and an acid value of 0.05.

The raw materials, catalysts, process conditions, and results of the examples and the comparative example are shown in Table 1 below.

TABLE 1

|  | Example | | | | | Comparative Example | | |
|---|---|---|---|---|---|---|---|---|
|  | 1 | 2 | 3 | 4 | 5 | 1 | 2 | 3 |
| 2-EH (g) | 1333.2 | 1333.2 | 1333.2 | 800 | 1333.2 | 1000.0 | 600.2 | 1333.2 |
| PTA (g) | 531.5 | 531.5 | 531.5 | 319 | 531.5 | 531.5 | 319 | 531.5 |
| DOTP (g) |  |  |  | 746 |  |  | 613 |  |

TABLE 1-continued

| | Example | | | | | Comparative Example | | |
|---|---|---|---|---|---|---|---|---|
| | 1 | 2 | 3 | 4 | 5 | 1 | 2 | 3 |
| Catalyst (Ti ppm) | | | | | | | | |
| TYZOR PC-64 | 82 | | | 82 | | | | |
| TYZOR TE | | 82 | | | | | | |
| TYZOR IAM | | | 82 | | 82 | | | |
| Tytan TnBT | | | | | | 280 | 165 | 280 |
| Pressure (Kg/cm2) | 4 | 4 | 3 | 4 | 4 | normal | normal | 4 |
| Filled distillation column | Yes | No | Yes | Yes | No | Yes | Yes | Yes |
| Esterification time (hr) | 5.3 | 3.7 | 4.0 | 4.3 | 2.7 | 5.0 | 4.4 | 6.0 |
| Quality of the plasticizer | | | | | | | | |
| Filtration time (500 g) | 45 m 39 s | 9 m 17 s | 4 m 05 s | 10 m 12 s | 6 m 43 s | 57 m 38 s | 135 m 30 s | 131 m 0 s |
| Hue (APHA) | 12 | 22 | 25 | 20 | 30 | 45 | 45 (cloudy) | 35 (cloudy) |
| Acid value(mg KOH/g) | 0.03 | 0.08 | 0.08 | 0.06 | 0.08 | 0.10 | 0.10 | 0.05 |

The method according to the present invention becomes clear by means of the aforesaid examples and comparative example. Using the chelated catalyst as the catalyst for alcoholization, the esterification rate and the filter efficiency are increased, and additionally, di(2-ethylhexyl) terephthalate with a hue of less than APHA 30 and an acid value of less than 0.1 mg KOH/g is obtained. In contrast, the comparative example does not use the chelated catalyst of the present invention as the alcoholysis catalyst, and as a result, the resultant di(2-ethylhexyl) terephthalate has high hue and the esterification and filtering take a long period of time. Additionally, it is known by comparing Examples 2 and 5, and Examples 1, 3, and 4 that, the method of the present invention can achieve the same efficacy using simple equipment instead of distillation column.

The addition of distillation column increases the manufacturing cost of reactor by about 20-30%. Nevertheless, the esterification between acid and alcohol using the $Ti(OR)_4$ catalyst of the prior art must be carried out in a reactor equipped with a distillation column. Otherwise, the catalyst will be hydrolyzed and deactivated, and the esterification time will be as long as 30-40 hrs. In contrast, according to the present invention, the esterification between acid and alcohol is carried out in the presence of a chelated catalyst, so that di(2-ethylhexyl) terephthalate with excellent hue and acid value can be obtained without distillation column, and as a result, the manufacturing cost is reduced.

What is claimed is:

1. A method for producing di(2-ethylhexyl) terephthalate, comprising:
    in an inert atmosphere, at a reaction pressure of higher than 1 atmosphere and a reaction temperature of 180-260° C., in the presence of a chelated catalyst of formula (I), subjecting terephthalic acid and 2-ethylhexanol to esterification, $$(RO)_m T\text{-}(O\text{---}Y\text{---}X)_n \qquad (I),$$

wherein in the formula (I), R is hydrogen or $C_1$-$C_8$ linear or branched alkyl, T is titanium or zirconium, Y is $C_2$-$C_3$ alkylene or a divalent phosphate radical, X is a functional group containing oxygen or nitrogen, m is an integer of 1 or 2, and n is an integer of 2 or 3.

2. The method of claim 1, wherein the 2-ethylhexanol is a pure 2-ethylhexanol or a 2-ethylhexanol recovered from the reaction that is not dehydrated.

3. The method of claim 1, wherein the molar ratio of the 2-ethylhexanol to the terephthalic acid is 2.6:1 to 4.0:1.

4. The method of claim 1, wherein the content of titanium or zirconium in the chelated catalyst is 20 ppm to 400 ppm relative to the total weight of the reactants.

5. The method of claim 1, wherein the reaction pressure is above 1 atmosphere to 4.0 kg/cm² gauge pressure.

6. The method of claim 3, wherein the molar ratio of the 2-ethylhexanol to the terephthalic acid is 3.0:1 to 3.5:1.

7. The method of claim 1, wherein the chelated catalyst is phosphate titanate chelate, triethanolamine titanate, or butyl titanium trialkoxyl phosphate dimer.

8. The method of claim 1, wherein the reactor is equipped with a condenser and an oil-water separator.

9. The method of claim 8, wherein the reactor is equipped with a return pipe, the mixture of water and alcohol produced by the esterification is condensed and separated in the oil-water separator, and the alcohol solution flows back to the reactor through the return pipe.

* * * * *